(12) United States Patent
Tam

(10) Patent No.: US 6,647,577 B2
(45) Date of Patent: Nov. 18, 2003

(54) ELECTRIC TOOTHBRUSH

(76) Inventor: Kwong Pui Tam, 5C, Skyscraper, 136 Tin Hau Temple Road, Hong Kong (HK)

( * ) Notice: Subject to any disclaimer, the term of this patent is extended or adjusted under 35 U.S.C. 154(b) by 71 days.

(21) Appl. No.: 10/092,785

(22) Filed: Mar. 7, 2002

(65) Prior Publication Data

US 2003/0167584 A1 Sep. 11, 2003

(51) Int. Cl.⁷ ............................. A61C 17/26; A46B 13/02
(52) U.S. Cl. ........................................................ 15/28
(58) Field of Search ...................... 15/22.1, 23, 24, 15/28, 29

(56) References Cited

U.S. PATENT DOCUMENTS

| 4,827,552 A | 5/1989 | Bojar et al. ................... 15/28 |
|---|---|---|
| 5,173,983 A | 12/1992 | Le .................................. 15/28 |
| 5,974,613 A | 11/1999 | Herzog ........................ 15/22.1 |
| 6,092,252 A | 7/2000 | Fischer et al. ............... 15/22.1 |
| 6,347,425 B1 | 2/2002 | Fattori et al. ................ 15/22.1 |

FOREIGN PATENT DOCUMENTS

| DE | 1062212 | 1/1958 | ..................... 15/23 |
|---|---|---|---|
| FR | 1137754 | 1/1957 | ..................... 15/23 |

*Primary Examiner*—Mark Spisich
(74) *Attorney, Agent, or Firm*—Gordon & Jacobson, P.C.

(57) ABSTRACT

An electric toothbrush includes a handle, a neck having a longitudinal axis and a brush head mounted to the neck and including bristles that rotate about an axis that is at an acute angle with respect to the longitudinal axis of the neck. Upon activation of a motor, the bristles rotate about the acute axis and tips of the bristles always move in a direction away from the user's gumline.

4 Claims, 5 Drawing Sheets

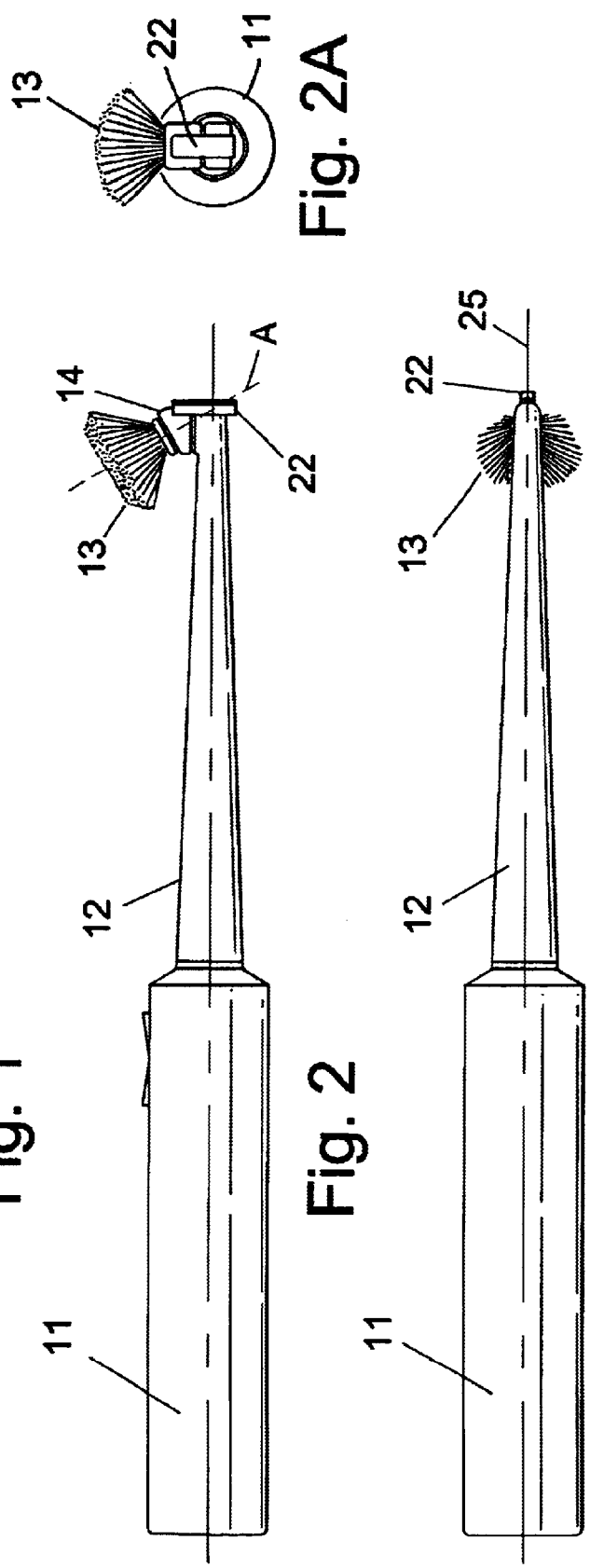

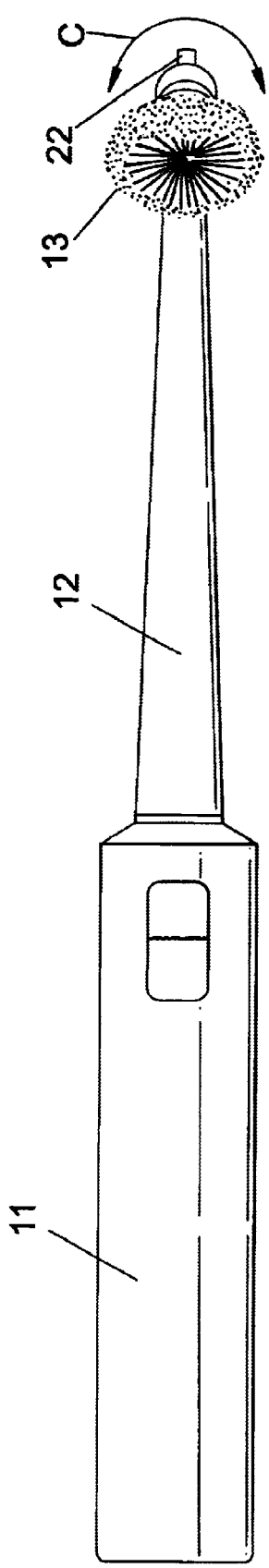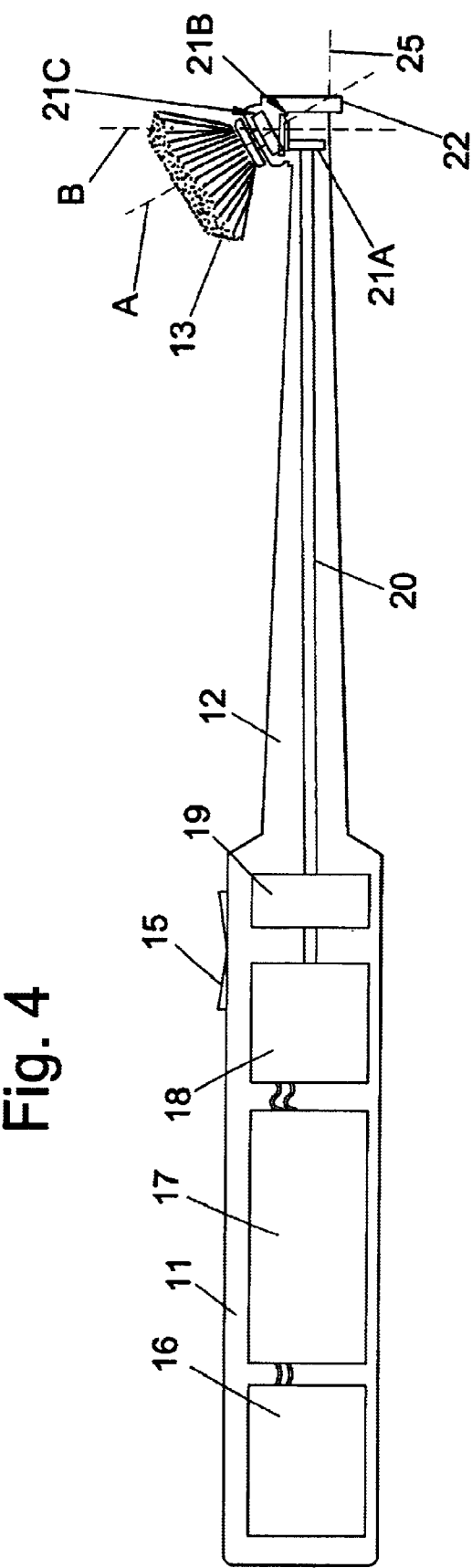
Fig. 4
Fig. 5

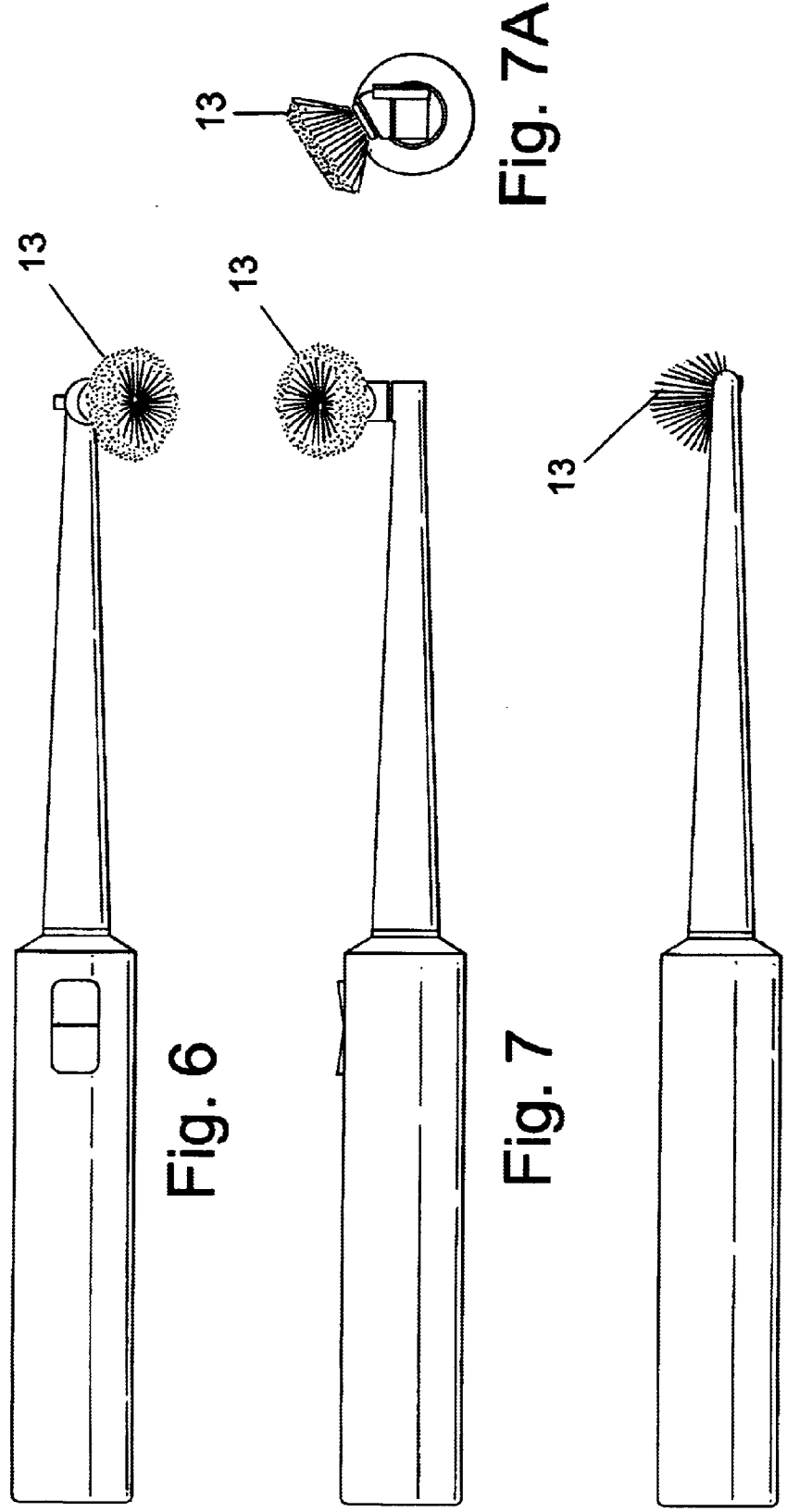

ELECTRIC TOOTHBRUSH

BACKGROUND OF THE INVENTION

1. Field of the Invention

The present invention relates to electric toothbrushes. More particularly, though not exclusively, the invention relates to an electric toothbrush having bristles arranged to brush away from the gumline and to brush the gaps between the teeth.

2. State of the Art

Modern electric toothbrushes often have a tuft of bristles that rotate continuously about an axis or pivot back and forth about an axis. The axis extends in a direction normal to the longitudinal axis of the toothbrush neck and body. This type of bristle movement can force food particles and plaque under the gumline and thereby promote gum disease, or other oral problems.

SUMMARY OF THE INVENTION

It is an object of the present invention to overcome or substantially ameliorate the above disadvantage and/or more generally to provide an improved electric toothbrush having bristles that provided cleaning action away from the gumline and to brush the gaps between the teeth.

There is disclosed herein an electric toothbrush comprising a handle, a neck having a longitudinal axis and a brush head mounted to the neck and including bristles that rotate about an axis that is at an acute angle with respect to the longitudinal axis of the neck.

Preferably the brush head has bristles positioned about said acute axis.

Preferably central ones of the bristles extend substantially parallel to said acute axis and other bristles positioned radially outwardly of said acute axis are angled outwardly therefrom.

Preferably the brush head is mounted to the neck so as to be selectively pivotable about an axis that is substantially normal to the longitudinal axis of the neck.

Preferably the toothbrush includes a motor-driven shaft within the neck and a gear arrangement transmitting rotation of the shaft to the head and bristles.

Preferably the gear arrangement includes a pinion mounted to the motor-driven shaft and an intermediate bevel gear meshing with the pinion and rotating about an axis substantially normal to the longitudinal axis of the neck, and a brush head bevel gear rotating about said acute axis and meshing with the intermediate bevel gear.

BRIEF DESCRIPTION OF THE DRAWINGS

A preferred form of the present invention will now be described by way of example with reference to the accompanying drawings, wherein:

FIG. 1 is a schematic plan view of a toothbrush,

FIG. 2 is a schematic elevational view of the toothbrush of FIG. 1,

FIG. 2A is a schematic end elevational view of the toothbrush of FIGS. 1 and 2,

FIG. 3 is a schematic inverted plan view of the toothbrush of FIGS. 1 and 2,

FIG. 4 is a schematic plan view of the toothbrush of FIGS. 1 to 3,

FIG. 5 is a schematic cross-sectional elevational view of the toothbrush of FIG. 4, FIG. 6 is a schematic plan view of the toothbrush with the brush head in a different configuration, FIG. 7 is a schematic elevational view of the toothbrush and brush head configuration of FIG. 6, FIG. 7A is a schematic end elevational view of the toothbrush of FIG. 7, FIG. 8 is a schematic inverted plan view of the toothbrush of FIG. 6.

DESCRIPTION OF THE PREFERRED EMBODIMENT

Figure 9A:
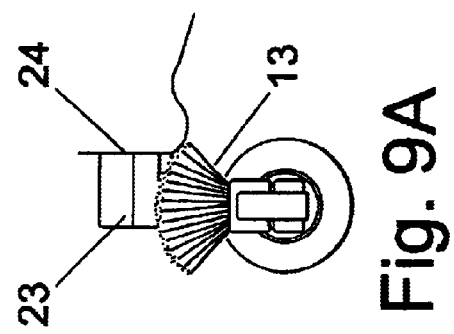
FIG. 9A is a schematic end elevational view of the toothbrush of FIG. 9 in use.

Referring to FIGS. 1 through 4, there is schematically depicted a toothbrush 10. Toothbrush 10 includes a handle 11 and a neck 12 to which there is mounted a brush head 14. Handle 11 and neck 12 would typically be formed of moulded plastics material. The handle portion 11 includes a switch 15.

The neck portion 12 includes a longitudinal axis 25. The bristles 13 are driven to rotate about an axis A that extends at an acute angle with respect to the longitudinal axis 25.

The head 14 includes a tab 22 by which the head 14 can be selectively pivoted about an axis B (FIG. 5).

As shown in FIG. 5, the handle 11 houses a battery charger 16, a battery 17, an electric motor 18 and a gearbox 19. The handle 11 might typically be placed in a cradle for recharging purposes, which cradle would include an electric coil that would surround the charger to induce current therein via magnetic flux. The charger charges the battery that powers the motor upon activation of switch 15.

Extending from the gearbox 19 is a driveshaft 20 which passes through the neck 12 to the head 14. Beneath the head 14 there is provided a pinion gear 21A that is attached to the driveshaft 20. The pinion gear meshes with an intermediate bevel gear 21B that rotates about an axis that is normal to the longitudinal axis 25. Meshing with the intermediate bevel gear 21B is a brush head bevel gear 21C. Brush head bevel gear 21C rotates about axis A. The bevel gear 21C is fixed with respect to the bristles 13. That is, both the bevel gear 21C and bristles rotate together about axis A.

When it is desired to change the position of the bristles 13, the tab 22 is moved in the directions indicated by arrow C in FIG. 4. For example, the bristles 13 can be moved into the configuration shown in FIGS. 6 through 8. This results in bevel gear 21C moving about the axis B in a planetary fashion whereby its teeth remain in contact with the teeth of intermediate bevel gear 21B. The bevel gears might be formed of plastics materials such as nylon, or might be metallic and can be mounted in suitable bearing for example. The bearings might simply be holes in the moulding from the brush head is formed.

Figure 9:
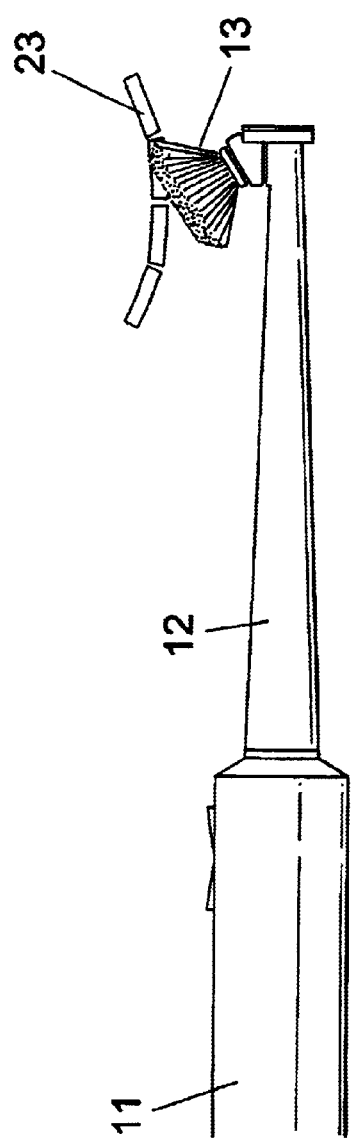
FIG. 9 is a schematic plan view of the toothbrush of FIG. 2 in use.
Figure 10:
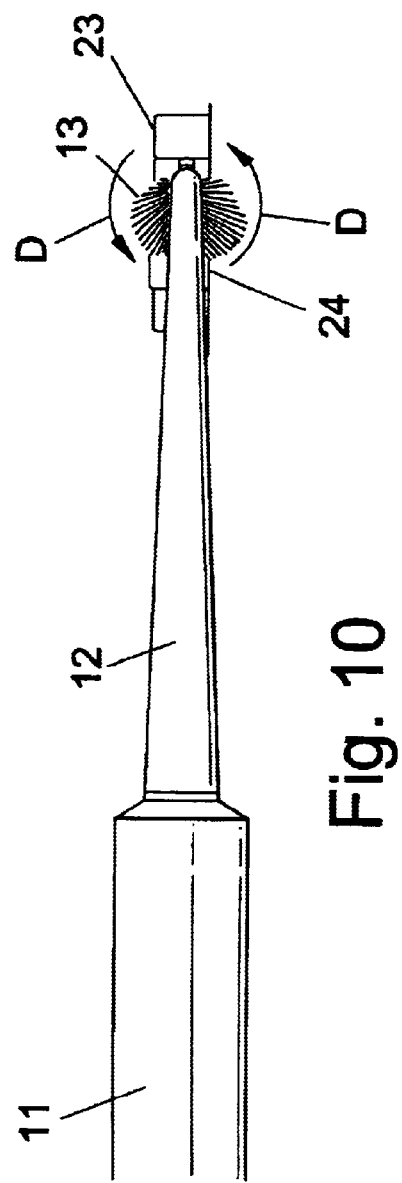
FIG. 10 is a schematic elevational view of the toothbrush of FIGS. 9 and 9A in use.

In use, the switch 15 is activated whereupon the bristles 13 begin to rotate about axis A. The tips of the bristles (perhaps with toothpaste pre-applied) are then brought into contact with the teeth 23 as shown in FIGS. 9, 9A and 10. The bristles move in the direction indicated by arrows D in FIG. 10, always away from the gumline 24. In order to clean other teeth, the brush head can be pivoted into another position by manipulation of tab 22.

Figure 11:
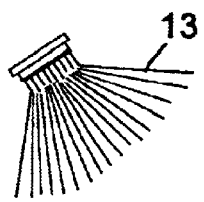
FIGS. 11 to 24 are schematic illustrations of alternative bristle configurations.
Figure 12:
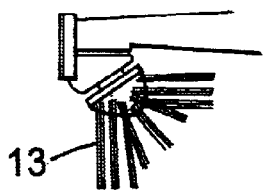
Figure 13:
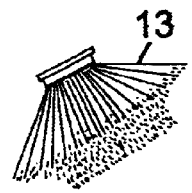
Figure 14:
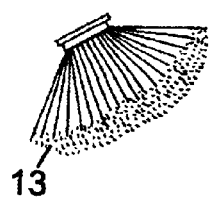
Figure 15:
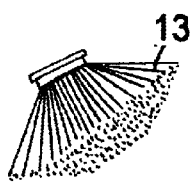
Figure 16:
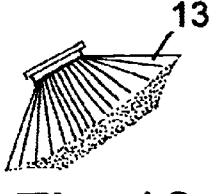
Figure 17:
Figure 18:
Figure 19:
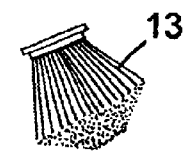
Figure 20:
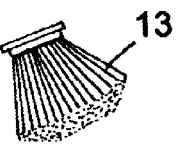
Figure 21:
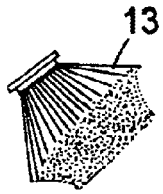
Figure 22:
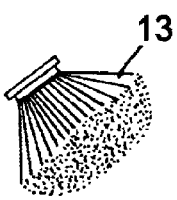
Figure 23:
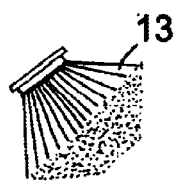
Figure 24:
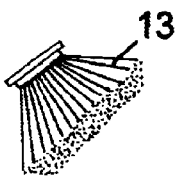

A number of different types of brush heads can be provided and a sample of these is shown in FIGS. 11 through to 24. The bristles may be provided in different levels of stiffness, high or low density packing and different tip configurations as shown.

It should be appreciated that modifications and alterations obvious to those skilled in the art are not to be considered as beyond the scope of the present invention. For example, the manual means of altering the configuration of the brush head might be replaced with switch-actuated means so that the user need not touch the brush head in use. That is, a "reconfigure" switch might be provided on the handle and a mechanism, perhaps including solenoids might be employed to swivel the brush head when it is desired to clean teeth in different positions.

Switch 15 or an additional switch might be provided to control and change the rotational direction of the bristles through a change in the direction of the current supplied to the electric motor or a change in the gearbox.

The neck and the brush head might be separately assembled into an article removable from the handle and reattachable into the handle by snapping or screwing onto the handle. The shaft and the gearbox might then be connected by a pair of meshing gears or similar plug-in joints.

In addition, the central bristles of the brush head might be trimmed, not provided for or positioned radially outwardly of said acute axis A and angled outwardly therefrom similar to the rest of the bristles.

What is claimed is:

1. An electric toothbrush comprising a handle, a neck having a longitudinal axis and a brush head mounted to the neck and including bristles that rotate about an axis that is at an acute angle with respect to the longitudinal axis of the neck, a motor-driven shaft within the neck and a gear arrangment transmitting rotation of the shaft to the head and bristles, wherein the gear arrangment include a pinion mounted to the motor-driven shaft and an intermediate bevel gear meshing with the pinion and rotating about an axis substantially normal to the longitudinal axis of the neck, and a brush head bevel gear rotating about said acute axis and meshing with the intermediate bevel gear.

2. The toothbrush of claim 1 wherein the brush head has bristles positioned about said acute axis.

3. The toothbrush of claim 2 wherein central ones of the bristles extend substantially parallel to said acute axis and other bristles positioned radially outwardly of said acute axis are angled outwardly therefrom.

4. The toothbrush of claim 1 wherein the brush head is mounted to the neck so as to be selectively pivotable about an axis that is substantially normal to the longitudinal axis of the neck.

* * * * *